US005556779A

United States Patent [19]
Khindaria et al.

[11] Patent Number: 5,556,779
[45] Date of Patent: *Sep. 17, 1996

[54] COMPOUNDS AND METHODS USEFUL FOR REDUCTIVE DEHALOGENATION OF ALIPHATIC HALOCARBONS

[75] Inventors: Aditya Khindaria, Logan; Thomas A. Grover, Hyde Park; Steven D. Aust, North Logan, all of Utah

[73] Assignee: Utah State University Foundation, Logan, Utah

[*] Notice: The term of this patent shall not extend beyond the expiration date of Pat. No. 5,389,356.

[21] Appl. No.: 388,252

[22] Filed: Feb. 13, 1995

Related U.S. Application Data

[63] Continuation-in-part of Ser. No. 1,106, Jan. 5, 1993, Pat. No. 5,389,356.
[51] Int. Cl.$^6$ .................................. C12P 3/00; C02F 3/02
[52] U.S. Cl. .................. 435/192; 435/168; 435/262; 435/262.5; 435/911; 423/659; 588/206; 588/901
[58] Field of Search ...................... 423/659; 588/206, 588/901; 435/262, 262.5, 264, 911, 168, 192

[56] References Cited

U.S. PATENT DOCUMENTS

| | | | |
|---|---|---|---|
| 3,888,890 | 6/1975 | Kirchner et al. | 260/369 |
| 3,923,966 | 12/1975 | Vaughan | 423/573 |
| 3,998,936 | 12/1976 | Ernst et al. | 423/588 |
| 4,102,950 | 7/1978 | Pilipovich et al. | 823/910 |
| 4,318,895 | 3/1982 | Richardson et al. | 423/579 |
| 4,533,443 | 8/1985 | Wrighton et al. | 204/84 |
| 4,554,075 | 11/1985 | Chang et al. | 210/611 |
| 4,629,690 | 12/1986 | Weng et al. | 435/7 |
| 4,751,068 | 6/1988 | Bickar et al. | 423/437 |
| 4,891,320 | 1/1990 | Aust et al. | 435/262 |
| 4,959,135 | 9/1990 | Zenner et al. | 204/129 |
| 4,977,090 | 12/1990 | Hutterman et al. | |
| 5,143,710 | 9/1992 | Sawyer et al. | 423/581 |
| 5,389,356 | 2/1995 | Aust et al. | 435/262 |
| 5,468,628 | 11/1995 | Aust et al. | 435/192 |

OTHER PUBLICATIONS

Shah, Manish M., et al., "Use of White Rot Rungi in the Degradation of Enfironmental Chemicals", Toxicology Letters, pp. 1–9, 1992.

Shah, Manish M., et al., "On the Mechanism of Inhibition of the Veratryl Alcohol Oxidase Activity of Lignin Peroxidase H2 by EDTA", The Journal of Biological Chemistry, vol. 267, No. 30, pp. 21564–21569, Oct. 30, 1992.

Shah, Manish M., et al., "Oxidation of Halides by Peroxidases and their Subsequent Reductions", Archives of Biochemistry and Biophysics, vol. 300, No. 1, pp. 001–005, 1993.

Barr, David P., et al., "Production of Hydroxyl Radical by Lignin Peroxidase from Phanerochaete Chrysosporium", Archives of Biochemistry and Biophysics, vol. 298, No. 2, pp. 480–484, Nov. 1, 1992.

Barr, David, P., et al., "Veratryl Alcohol—Dependent Production of Molecular Oxygen by Lignin Peroxidase", The Journal of Biological Chemistry, vol. 268, No. 5, pp. 1–4, 1993.

Popp, Janet L., et al. "Lignin Peroxidase Oxidation of $mN^{2+}$ in the Presence of Veratryl Alcohol, Malonic or Oxalic Acid, and Oxygen", vol. 29, pp. 10475–10480, Jun. 1990.

*Primary Examiner*—Herbert J. Lilling
*Attorney, Agent, or Firm*—Workman Nydegger Seeley

[57] ABSTRACT

This invention describes a method for catalyzing sequential reductive dehalogenation reactions on aliphatic halocarbons using free radical intermediates. More specifically, this invention involves the use of biologically derived peroxidases in the generation of a variety of oxidation or reduction agents consisting of cation radicals, anion radicals, neutral radicals, or oxygen radicals. Such oxidation and reduction agents can be employed in combination to carry out sequential reductive dehalogenation reactions on aliphatic halocarbons to thereby degrade various recalcitrant organic compounds such as organic environmental pollutants.

35 Claims, 5 Drawing Sheets

COMPOUNDS AND METHODS USEFUL FOR REDUCTIVE DEHALOGENATION OF ALIPHATIC HALOCARBONS

GRANT INFORMATION

This work was supported by a grant from the National Institute of Health, Grant No. ES04922.

RELATED APPLICATIONS

This application is a continuation-in-part of Ser. No. 08/001,106, filed Jan. 5, 1993, which will issue as U.S. Pat. No. 5,389,356 on Feb. 14, 1995.

BACKGROUND OF THE INVENTION

Field of the Invention

This invention describes a method for catalyzing sequential reductive dehalogenation reactions on aliphatic halocarbons using free radical intermediates. More specifically, this invention involves the use of biologically derived peroxidases in the generation of a variety of oxidation or reduction agents consisting of cation radicals, anion radicals, neutral radicals, or oxygen radicals. Such oxidation and reduction agents can be employed in combination to carry out sequential reductive dehalogenation reactions on aliphatic halocarbons to thereby degrade various recalcitrant organic compounds such as organic environmental pollutants.

The Relevant Technology

The use of oxidation or reducing agents to carry out oxidations or reductions on targeted substrates is mature technology well-known in the art. Desired oxidation and reduction reactions can be carried out on a multitude of different substrates simply by reacting the substrate with a stoichiometrically adequate amount of an appropriate oxidant or reductant. Commonly used oxidants or reductants which can be produced in a commercially feasible manner include a wide variety of generally inorganic agents. The feasibility of using such oxidants or reductants is often limited by such restraints as the cost of the reactant in relation to the value of the reacted substrate, the ability to control the reaction, and the ability to obtain suitable concentrations of the reacted substrate in reasonably pure amounts.

More complicated oxidation and/or reduction reactions have been created which involve organic intermediates, such as hydroquinones, alkylanthraquinones, anilines, hydrazines, or metal complexed chelating agents. In some cases, the reactant is a catalyst which is continuously regenerated. For example, U.S. Pat. No. 5,143,710 to Sawyer et al. discloses methods for generating superoxide ions in situ catalyzed by aniline, N-substituted aniline compounds, or phenylhydrazine compounds. The superoxide ion, which is an anion radical, is useful for a number of different applications discussed within Sawyer et al. Superoxide ions have proven particularly effective in destroying a variety of halogenated hydrocarbons such as polychlorinated biphenyls ("PCBs") and similar toxic materials. In general, superoxide ions are useful reducing agents.

U.S. Pat. No. 3,998,936 to Ernst et al. discloses a process for regenerating the activity of the catalyst used in the hydrogenation (or reduction) stage of the cyclic anthraquinone process for producing hydrogen peroxide involving the use of a platinum group metal catalyst. However, Ernst et al. does not disclose how an overall oxidation/reduction system could be constructed that would have broad application.

U.S. Pat. No. 4,751,068 to Bicker et al. discloses a method of catalyzing oxidation/reduction reactions of simple molecules through the redox catalytic activity of chelating agents complexed with a metal atom (the complex being referred to as a "chelate"). These chelates have been shown to be useful in converting CO and $H_2O$ to $CO_2$, CO and $H_2S$ to COS, CS and $H_2S$ to $CS_2$, CO and $NH_3$ to CONH, and CO and $RNH_2$ to RNCO. However, in order to regenerate the spent chelates it is necessary to react the chelates with oxidants or reductants. No self-sustaining reaction sequence is disclosed in Bicker et al.

More recently, with the advent of more refined biochemical techniques, biologically induced oxidations and reductions have been carried out using, e.g., fungi and agents which are secreted thereby. These biologically derived reactions are often superior to simply adding oxidation and/or reducing agents to a reaction mixture because of their lower cost and greater ability to more carefully control the reaction conditions, especially those reactions which involve the use of enzymes. Enzymes have the advantage of being able to overcome high reaction barriers without the input and/or generation of large amount amounts of energy such as heat. In addition, as long as the biological agent is kept alive by ensuring that the system has adequate quantities of nutrients (some or all of which are supplied by the chemicals targeted for degradation) it will continue to produce adequate quantities of the oxidation or reduction agents. In this manner, the reaction is often self-sustaining so that no new reactants need to be added to complete the oxidation and/or reduction reactions.

There are numerous examples of biologically induced degradation of organic molecules. For example, lignin, which is the structural polymer found in wood and a substance which is otherwise highly resistant to many forms of biodegradation, is readily degraded in the presence of the white rot fungus Phanerochaete chrysosporium. Kirk, T. et al., *Arch. Microbiol.* 117:277–85 (1978). Lignin degradation is catalyzed by a group of enzymes including extracellular peroxidases secreted by *P. chrysosporium* under nutrient nitrogen-limiting conditions. Gold, M. et al., *Arch. Biochem. Biophys.*, 234:353–62(1984); Tien, M. et al., *Proc. Natl. Acad Sci. USA*, 81:2280–84 (1984). It is known that both lignin peroxidases ("LIP") and manganese-dependent peroxidases are produced by white rot fungi. Glenn, J. et al, *Arch. Biochem. Biophys.*, 242:329–41 (1985). The fungi also produce enzymes that generate hydrogen peroxide. Kelley, R. et al, *Arch. Microbiol.*, 144:248–53 (1986); Kersten, P., *Biochemistry*, 87:2936–40 (1990). Veratryl alcohol (3,4-dimethoxybenzyl alcohol) is a secondary metabolite of *P. chrysosporium* and is also believed to be involved in lignin degradation. Harvey, P. et al., *FEBS Lett.*, 195:242–46 (1985).

In addition, the degradation of several environmental pollutants to carbon dioxide by white rot fungi has also been reported. U.S. Pat. No. 4,891,320 to Aust et al; Bumpus, J. et al., *Science*, 228:1434–36; Ryan, T. et al., *Appl. Microbiol. Biotechnol.*, 31:302:07 (1989); Fernando, T. et al, *Appl. Microbiol. Biotechnol.*, 56:1666–71 (1990); Kennedy, D. et al., *Appl. Microbiol. Biotechnol.*, 56:2346–53 (1990). In particular, *P. chrysosporium* is known to mineralize lignin and a variety of environmental pollutants. Shoemaker, H. E., *Recl. Trav. Chim. Pays-Bas*, 109:255–272 (1990); Barr, D. P., et al., *Environ. Sci. Technol.*, 28:78A-87A (1994). A part of the lignin degrading system, consisting of lignin and manganese-dependent peroxidases, $H_2O_2$ generating enzymes, veratryl alcohol, and manganese, is, in part, responsible for degrading and mineralizing environmental pollutants. Aust, S. D., *Microb. Ecol.*, 20:197–209 (1990); Higson, F. K., *Rev. Environ. Contain. Toxicol.*, 122:111–141 (1991); Tien, M., *Crit. Rev. Microbiol.*, 15:141–168 (1987).

Lignin peroxidases are extracellular heine proteins secreted by the fungus. These are known to oxidize a wide variety of organic compounds. This oxidation involves the activation of the ferric enzyme, by $H_2O_2$, to a ferryl π-porphyrin cation radical known as compound I. Compound I can oxidize organic chemicals to cation radicals and is reduced to compound II. A subsequent one electron reduction reduces the enzyme to its native ferric state while another organic molecule is oxidized by one electron. Dunford, H. B., *Adv. Inorg. Biochem.*, 4:41–68 (1982). Hence, the typical peroxidase catalytic cycle results in two one-electron oxidations of the substrates.

In the last few decades, there has been growing concern about the accumulation of toxic organic pollutants in the soil and water. Many industrial operations, particularly those involving chemical processes, have resulted in the contamination of huge amounts of soil, which in turn pollutes ground water and streams. With the fairly recent passage of stricter environmental legislation mandating the cleanup of what are referred to as "remediation sites" there has arisen a great need for practical and economically viable methods of soil and water remediation.

In the case of toxic organic pollutants such as chlorinated hydrocarbons, PCBs, and other organic solvents, the primary method of removing these from the soil involves the temporary removal of the contaminated soil, which is then passed through large columns through which hot air is passed. This causes the volatile contaminants to be driven off by evaporation. However, not only is this method extremely expensive, it does not guarantee the removal of the pollutants from the environment but simply shifts them from the ground into the air. While some degradation of these pollutants may occur in the presence of sunlight, many of the less reactive compounds are simply scattered into the air where they might later precipitate back into the earth, albeit in a more diluted form.

Many xenobiotics introduced for industrial use are halogenated and this halogenation often makes these chemicals very persistent after their disposal. Halogenated organics are used as herbicides, plastics, solvents, and degreasers. Halogenated aliphatic compounds are prevalent as groundwater contaminants and are significant components of hazardous wastes and landfill leachates. Many hazardous halogenated aliphatic compounds released from industrial and agricultural sources are chlorinated or brominated alkanes or alkenes that contain one to three carbon atoms, such as trichlorethylene (TCE), trichloroethane (TCA), chloroform ($CHCl_3$), dichloromethane ($CH_2Cl_2$), and carbon tetrachloride ($CCl_4$). These have commonly been used as refrigerants, solvents in dry cleaning and lacquer industries, and in semiconductor manufacturing. Their apparent hazard to human health has prompted investigations concerning their fate in subsurface waters and soil.

Because of their highly oxidized nature, there is no evidence for the aerobic breakdown of TCE or $CCl_4$ in the literature. Mineralization under anaerobic conditions has been reported. Fogel, M. M., et al., *Appl. Environ. Microbiol.*, 51:720–724 (1986); Oldenhuis, R., et al., *Appl. Environ. Microbiol.*, 55:2819–2826 (1989); Vogel, T. M., et al., *Environ. Sci. Technol.*, 21:722–736 (1987). The incomplete reductive dechlorination of these halocarbons, resulting in accumulations of dichloroethene (DCE) and $CHCl_3$ or $CH_2Cl_2$, respectively, is of little or no benefit as these halocarbons are also regulated under the 1986 Safe Drinking Water Act Amendments, precisely because they too pose a threat to public health. It has been reported that mineralization in the range of 24% and 27% of low concentrations (31 to 60 µg/l) of an aliphatic halocarbon, perchloroethylene, occurred under anaerobic conditions. Vogel, T. M. et al., *Enviorn. Sci. Technol.*, 21:1208–1213 (1987); Vogel, T. M., et al., *Appl. Environ. Microbiol.*, 49:1080–1083 (1985). These concentrations, however, are insignificant when compared to the levels of contamination in the environment.

From the foregoing it should be understood that what are needed are compositions and methods which can be generally employed to carry out sequential reductive dehalogenation reactions capable of mineralizing environmental contaminant concentrations of aliphatic halocarbon pollutants to environmentally acceptable biotransformation products. Moreover, it will be appreciated that it would be a significant advancement of the art if such compositions and methods could be cheaply and easily carried out by using relatively inexpensive raw materials, such as those used to grow white rot fungi.

It would yet be a significant improvement over the prior art if such compositions and methods could be varied to alternatively reduce, oxidize, or both, depending on the substrates to be degraded. Specifically, it would be a major advancement in the art if both the oxidative and reductive properties could be carefully controlled so that compounds requiring both oxidation and reduction for their degradation can be fully degraded utilizing a single reactive system, or different systems or conditions in series.

It would yet be a significant improvement over the prior art to provide compositions and methods under a variety of conditions which could degrade a variety of recalcitrant environmental pollutants such as PCBs, chlorinated hydrocarbons, and other toxic organic wastes without having to physically alter the reaction conditions once the reactions are set in motion. In addition, because living organisms are typically employed to carry out these reactions, it would be a major advancement in the art if such compositions and methods resulted in the generation of sufficient molecular oxygen so that the organisms would stay alive even under extremely anaerobic conditions, such as in remediation sites where the organisms are injected deep into the contaminated soil.

Such compositions and methods are disclosed and claimed herein.

BRIEF SUMMARY OF THE INVENTION

The following abbreviations are used throughout this specification: TCE, 1,1,2-trichloroethylene; TCA, 1,1,1-trichloroethane; LiP, lignin peroxidase; VA, veratryl alcohol; PBN, α-phenyl-N-tert-butylnitrone; EDTA, ethylenediaminetetraacetic acid; DMPO, 5,5-dimethyl-1-pyrroline-N-oxide; ESR, electron spin resonance spectroscopy; NHE, normal hydrogen electrode.

It is an object of the present invention to provide compositions and methods which can be generally employed to carry out sequential reductive dehalogenation reactions capable of mineralizing environmental contaminant concentrations of aliphatic halocarbon pollutants to environmentally acceptable biotransformation products.

It is a further object of the present invention to provide such compositions and methods using relatively inexpensive raw materials, such as those used to grow white rot fungi.

It is yet another object of the present invention to provide compositions and methods which could be carefully controlled so that compounds requiring both oxidation and reduction for their degradation can be fully degraded utilizing a single reactive system, or different systems or conditions in series.

This invention describes a method for catalyzing sequential reductive dehalogenation reactions on aliphatic halocarbons using free radical intermediates. More specifically, this invention involves the use of biologically derived peroxidases in the generation of a variety of oxidation or reduction agents consisting of cation radicals, anion radicals, neutral radicals, or oxygen radicals. Such oxidation and reduction agents can be employed in combination to carry out sequential reductive dehalogenation reactions on aliphatic halocarbons to thereby degrade various recalcitrant organic compounds such as organic environmental pollutants.

White rot fungi, such as *Phanerochaete chrysosporium*, are known for their ability to degrade lignin to carbon dioxide. Some of the important components of the lignin degrading enzyme system of the fungi are lignin peroxidases, manganese-dependent peroxidases, veratryl alcohol, manganese, oxalate and $H_2O_2$. Because chlorinated organic materials are highly electron deficient they cannot be oxidized by the enzyme or the free radical of the mediator. For the reductive dehalogenation of these chemicals, reducing reaction conditions are required. It has been discovered that TCE, $CCl_4$, and other very highly oxidized halocarbons can be reductively dehalogenated and the reduced products mineralized by ligninolytic cultures of *P. chrysosporium*.

According to the present invention it has been discovered that LiP is apparently able to catalyze reduction reactions using organic acids like EDTA or oxalate as a reductant and veratryl alcohol as a free radical mediator. It is also possible that oxidized manganese mediates the oxidation of oxalate. Studies have demonstrated that the veratryl alcohol cation radical can oxidize organic acids such as EDTA and oxalate to their anion radicals. It has been discovered that oxalate, a secondary metabolite of *Phanerochaete chrysosporium*, can act as an electron donor and mediate reductive dehalogenation. It has further been discovered that chemicals with high reduction potentials, like $CHCl_3$, can be dehalogenated by this mechanism. Mineralization of highly oxidized and electron deficient compounds is presented as evidence for possible involvement of these reductive reactions in vivo.

It has been discovered that, not only a good electron acceptor like $CCl_4$, but halocarbons like $CHCl_3$, TCE or TCA, can be reductively dechlorinated by this mechanism. In the experiments reported below, dehalogenated radicals, arising from homolytic C—Cl bond cleavage of these halocarbons, were detected by ESR spin trapping. This reductive dehalogenation is a free radical mediated process, which may be initiated by the oxidation of veratryl alcohol to the veratryl alcohol cation radical. The veratryl alcohol cation radical could oxidize an organic acid reductant to form the anion radical of the reductant. The anion radicals of either EDTA or oxalate can be further oxidized during the next reactive step with an electron acceptor and decarboxylated. In this manner, either the EDTA radical or the carboxylate anion radical, respectively, would be generated which can reductively dehalogenate the aliphatic halocarbon. Alternatively, manganese, oxidized by the peroxidases, can be used to oxidize oxalate to bring about reductive dehalogenation.

DETAILED DESCRIPTION OF THE PREFERRED EMBODIMENTS

Figure 1A:
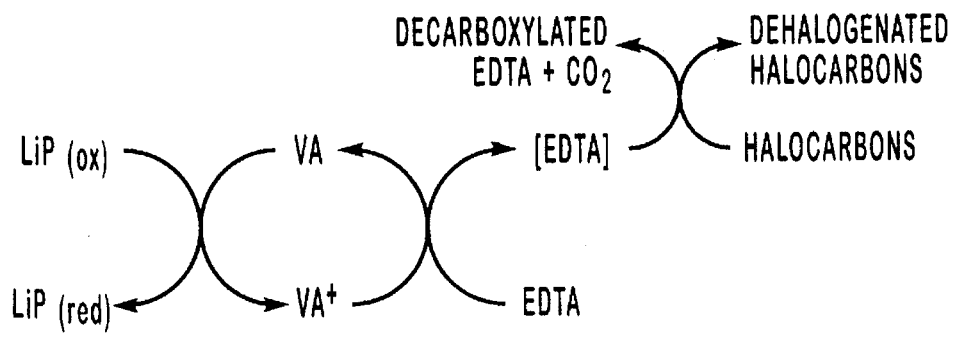
FIG. 1A illustrates a proposed reaction sequence for reductive dehalogenation of aliphatic halocarbons by lignin peroxidase using EDTA as an electron donor.

The following abbreviations are used throughout this specification: TCE, 1,1,2-trichloroethylene; TCA, 1,1,1-trichloroethane; LiP, lignin peroxidase; VA, veratryl alcohol; PBN, α-phenyl-N-tert-butylnitrone; EDTA, ethylenediaminetetraacetic acid; DMPO, 5,5-dimethyl-1-pyrroline-N-oxide; ESR, electron spin resonance spectroscopy; NHE, normal hydrogen electrode.

White rot fungi, such as *Phanerochaete chrysosporium*, are known for their ability to degrade lignin to carbon dioxide. Some of the important components of the lignin degrading enzyme system of the fungi are lignin peroxidases, manganese-dependent peroxidoses, veratryl alcohol, manganese, oxalate, and $H_2$ $O_2$. In addition to lignin, the fungi are known to mineralize a variety of recalcitrant chemicals such as $CCl_4$, DDT, TCDD, Lindane, and PCBs to carbon dioxide. Although white rot fungi were previously shown to be able to degrade halogenated chemicals, the mechanism was heretofore never understood. Hence, controlled, sustainable reactions could not be carried out on a large scale, such as under conditions relating to the remediation of toxic waste sites. In particular, dehalogenation by LiP alone has never been demonstrated. In fact, LiP has been reported to be a haloperoxidase. Ranganathan, V. et al., *Biochemstry* 26:5127–32 (1987); Farhangrazi Z. et al., *Biochemstry* 31:10763–68 (1992).

Therefore, the focus of most researchers has been towards the oxidative reactions of LiP instead of the reductive reactions of LiP of the present invention. Because chlorinated organic materials are highly electron deficient they cannot be oxidized by the enzyme or the free radical of the mediator. For the reductive dehalogenation of these chemicals, reducing reaction conditions are required. According to the present invention it has been discovered that LiP is apparently able to catalyze reduction reactions using organic acids like EDTA or oxalate as a reductant and veratryl alcohol as a free radical mediator. Shah, M. et al., On the Mechanism of Inhibition of the Veratryl Alcohol Oxidase Activity of Lignin Peroxidase H2 by EDTA, *J. Biol. Chem.*, 267:21564–69 (October 1992); Barr, D. et al., Production of Hydroxyl Radical by Lignin Peroxidase From Phanerochaete chrysosporium, *Arch. Biochem. Biophys.*, 298:480–85 (November 1992). It is also possible that manganese, oxidized by the enzymes, mediates the oxidation of oxalate.

In the case of chlorinated hydrocarbons, the molecules must first be reduced to remove the chlorine moieties (which are reduced to chloride ions). It has been shown that a reaction sequence could specifically be designed which would reduce $CCl_4$ to trichloromethyl radical (which is then degraded to $CO_2$). Once the chlorine moieties have been removed from the chlorinated hydrocarbon, the remaining carbon-containing molecules are easily oxidized to $CO_2$ by means of the free radical of the mediator. Shah, M. et al, Oxidation of Halides by Peroxidases and Their Subsequent Reactions, *Arch. Biochem. Biophys.*, 300:001–005 (Jan. 1993). For purposes of disclosure this article is incorporated herein by specific reference.

It has previously been shown that organic cation radicals, like the veratryl alcohol cation radical, can initiate free radical reactions leading to oxidation of other chemicals and reduction of some chemicals by these enzymes. Popp, J. L., et al., *Biochemistry* 29:10475–10480 (1990), Shah, M. M., et al., *Biochem. Biophys. Res. Commun.*, 191:887–892 (1993); Shah, M. M., et al., *J. Biol. Chem.*, 268:8503–8506 (1993). Studies have demonstrated that the veratryl alcohol cation radical can oxidize organic acids such as EDTA and oxalate to their anion radicals. These organic acid anion radicals can then reduce nitroblue tetrazolium, cytochrome c, molecular oxygen and carbon tetrachloride.

It has been discovered that oxalate, a secondary metabolite of *Phanerochaete chrysosporium*, can act as an electron donor and mediate reductive dehalogenation. It has further been discovered that chemicals with high reduction potentials, like $CHCl_3$, can be dehalogenated by this mechanism. Mineralization of highly oxidized and electron deficient compounds is presented as evidence for possible involvement of these reductive reactions in vivo.

General agreement exists that transformation of aliphatic halocarbons under anaerobic conditions proceeds by sequential reductive dechlorination. An auxiliary electron donor is needed to sustain this reductive dechlorination. Freedman, D. L., et al., *Appl. Environ. Microbiol.*, 55:2144–2151 (1989). The major argument against reductive dechlorination under aerobic conditions is that dioxygen would appear to be the favored electron acceptor. However, highly oxidized and electron deficient compounds can compete with dioxygen for reducing equivalents. Several investigators have shown that, under aerobic conditions, homolytic cleavage of the C—Cl bond in halocarbons results from free radical attack. Moreover, reduction of $CCl_{14}$ to the trichloromethyl radical in the presence of dioxygen and an organic acid (EDTA as electron donor) has been demonstrated. Shah, M. M., et al., *Biochem. Biophys. Res. Commun.*, 191:887–892 (1993). It has been discovered that, not only a good electron acceptor like CCl4, but halocarbons like $CHCl_3$, TCE or TCA, can be reductively dechlorinated by this mechanism. In the experiments reported below, dehalogenated radicals, arising from homolytic C—Cl bond cleavage of these halocarbons, were detected by ESR spin trapping.

This reductive dehalogenation is a free radical mediated process, possibly initiated by the oxidation of veratryl alcohol to the veratryl alcohol cation radical. Harvey, P. J., et al., *J. Biotechnol.*, 30:57–69 (1993). It is also possible that $Mn^{+2}$ is oxidize to $Mn^{+3}$. Veratryl alcohol cation radical or $Mn^{+3}$ in turn oxidize EDTA or oxalate (excreted extracellularly by the fungus) to their respective radicals. Oxalate is decarboxylated with release of $CO_2^-$ anion radical. Popp, J. L., et al., *Biochemstry* 29:10475–10480 (1990); Shah, M. M., et al., *J. Biol. Chem.*, On the Mechanism of Inhibition of the Veratryl Alcohol Oxidase Activity of Lignin Peroxidase H2 by EDTA, *J. Biol.*, 267:21564–69 (October 1992). For purposes of disclosure this article is incorporated herein by specific reference.

It is believed that either the EDTA radical or the carboxylate anion radical derived from either EDTA or oxalate, respectively, can reductively dehalogenate the aliphatic halocarbon. A proposed reaction sequence for reductive dehalogenation of the aliphatic halocarbon by lignin peroxidase using EDTA as the electron donor is shown in FIG. 1A. A proposed reaction sequence for reductive dehalogenation of the aliphatic halocarbon by lignin peroxidase using oxalate as the electron donor is shown in FIG.1B.

Figure 1B:
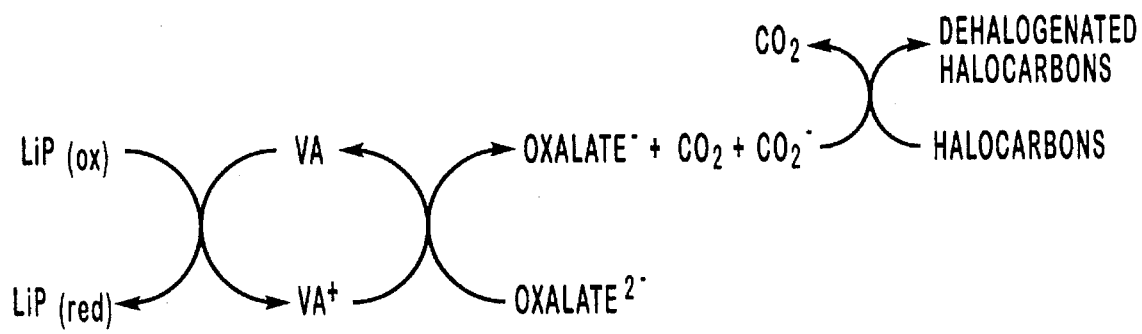
FIG. 1B illustrates a proposed reaction sequence for reductive dehalogenation of aliphatic halocarbons by lignin peroxidase using oxalate as an electron donor.

Referring to FIG. 1, the general reaction scheme of the present invention is as follows: Lignin peroxidase (LIP) is activated by hydrogen peroxide to an activated 2-electron deficient oxidized enzyme intermediate designated $LiPo_{(ox)}$ in FIG. 1. As shown, the activated LiP reacts with veratryl alcohol (VA) to form the veratryl alcohol cation radical ($VA^+$), a strong oxidant. Because the enzyme intermediate is deficient of two electrons, it will be appreciated that each mole of the enzyme intermediate is normally able to react with two moles of mediator to form two moles of the free radical of the mediator. Next, the veratryl alcohol cation radical oxidizes an organic acid reductant to form the anion radical of the reductant. The anion radicals of either EDTA or oxalate are further oxidized during the next reactive step with an electron acceptor and decarboxylated. As shown in FIG. 1A, the EDTA radical, designated [EDTA], reductively dehalogenates the aliphatic hydrocarbon in this decarboxylation reaction producing decarboxylated EDTA and $CO_2$. As shown in FIG. 1B, the oxalate radical, designated Oxalate, is decarboxylated with the release of carboxylate anion radical, shown as $CO_2^-$ and it is the carboxylate anion radical which then reductively dehalogenates the aliphatic halocarbon.

The reduction products of $CCl_4$ have been reported to include $CHCl_3$ and $CH_2Cl_2$. Shah, M. M., et al., *J. Biol. Chem.*, On the Mechanism of Inhibition of the Veratryl Alcohol Oxidase Activity of Lignin Peroxidase.H2 by EDTA, *J. Biol. Chem.*, 267:21564–69 (October 1992). Thus, it was important to determine that $CHCl_3$ and $CH_2Cl_2$ can be dehalogenated through reactions catalyzed by lignin peroxidase. Further confirmation of the identity of the radicals comes from the experiments described below in which identical ESR hyperfine splitting constants were obtained for the dichloromethyl and monochloromethyl radicals, generated by using two different reductants, EDTA and oxalate, and using different halocarbons, namely $CHCl_3$, $CHCl_2Br$, $CH_2Cl_2$, and $CH_2ClBr$. Additionally, the use of $^{13}C$-labeled isotopes of these halocarbons further confirmed the identity of the PBN-halocarbon radical adducts. These findings and others will be discussed in more detail following presentation of the experimental data.

EXPERIMENTAL DATA

I. Materials and Methods

Materials: Hydrogen peroxide, PBN, DMPO, Tempol, TCA, TCE, $CHCl_3$, $CH_2Cl_2$, $CHCl_2Br$ and $CH_2ClBr$ were obtained from Sigma Chemical Company (St. Louis, Mo.). Veratryl alcohol was purchased from Aldrich Chemical Company (Milwaukee, Wis.) and purified by distillation. EDTA was obtained from Mallinckrodt (Paris, Ky.). Chelex 100 resin was obtained from Bio-Rad Laboratories (Hercules, Calif.). Buffers and reagents were prepared with purified water (Barnstead Nanopure II system). Stable $^{13}C$-labeled isotopes of $CHCl_3$ and $CH_2Cl_2$ (99%) were obtained from Cambridge Isotope Laboratories (Andover, Mass.). Radiolabelled $[^{14}C]$-$CCl_4$ (99%, 4.1 mCi/mmol) was purchased from NEN Radiochemicals (Boston, Mass.) and $\alpha,\beta[^{14}C]$-TCE (99%, 5mCi/mmol) was purchased from Sigma Chemical Company (St. Louis, Mo.). All chemicals were used as purchased unless otherwise stated.

Lignin Peroxidase Production and Purification: Culture conditions for the production of lignin peroxidase from *P. chrysosporium* and its purification and assay were as previously described in Tuisel, H. et al, *Arch. Biochem. Biophys,* 279:158–66 (1990). For purposes of disclosure, this article is incorporated by specific reference. Lignin peroxidase isozyme H2 (55 U/mg, pI=4.3) was used for all the experiments.

Spin Trapping Experiments: Radicals were detected by electron spin resonance (ESR) spectroscopy as spin adducts with PBN. Reaction mixtures contained 0.1M CHELEX-treated sodium phosphate buffer, pH 6.0, 1 μM LiP, 1 mM veratryl alcohol, 500 μM $H_2O_2$, 80 mM PBN, and 1% of the halocarbon of interest. Emulsions of the halocarbons were prepared by mixing the halocarbon and the buffer with a vortex mixer before adding the other components of the reaction mixture. The total reaction volume was 300 μl. For ESR detection of the carboxylate anion radical, the spin trap DMPO was used. Where mentioned, the reaction mixture was purged with argon to provide anaerobic conditions. Spectral recordings were started within 1 minute following the initiation of reactions with $H_2O_2$. ESR spectra were recorded at room temperature using a Bruker ECS-106 ESR spectrometer operating at 9.8 GHz with 50 kHz modulation frequency and 50 mW microwave power except where other spectrometer settings are described. Hyperfine splitting constants were determined by comparison with the standard Tempol using 17.1 G for $a_N$ in water.

Mineralization of halocarbons: Cultures were set up in 250-mL sealed Wheaton bottles equipped with a gas-exchange manifold. Nutrient nitrogen (ammonia)-limited and nitrogen-sufficient cultures were as described previously. Tuisel, H. et al, *Arch. Biochem. Biophys,* 279:158–66 (1990). On day 5, after the nitrogen-limited cultures became ligninolytic as determined by veratryl alcohol oxidase activity, 100,000 dpm of $[^{14}C]$-$CCl_4$ or $\alpha,\beta[^{14}C]$-TCE and 10 ppm $CCl_4$ or TCE, respectively, were added as a solution in ethanol (10 μl). Controls contained 5 ml formaldehyde. Triplicate cultures were flushed with pure oxygen after 3, 6, or 9 days, and the $CO_2$ evolved during these time periods was trapped as described before, Bumpus, et al., *Appl. Environ. Microbiol.,* 52:2001–2008 (1987), except that three organic traps (Safety Solve Scintillation Cocktail, Research Products International Corp., Mt. Prospect, Ill.) were used in series before the $CO_2$ trap, (10% ethanolamine, 40% methanol, and 50% Safety Solve Scintillation Cocktail) to eliminate any carryover of volatile halocarbon to the $CO_2$ trap. Background radiation levels were observed in the last organic trap immediately preceding the $CO_2$ trap. The radioactivity evolved was determined by liquid scintillation spectrometry (Beckman, LS 5801) using 10 ml of Safety Solve Scintillation Cocktail. Radiolabeled $^{14}CO_2$ evolution was confirmed by precipitation with 1M $BaCl_2$. The $[^{14}C]$ $BaCO_3$ was quantitated by scintillation spectrometry. The mineralization data are presented as a percent of initial chemical added, corrected for the amount of chemical lost due to sorption or other abiotic processes during the incubation period. Fan, S., et al.,*Appl. Environ. Microbiol.,* 59:1911–1918 (1993). The amount lost was calculated by determining the radioactivity remaining in control (uninoculated) flasks. Losses were generally relatively low as mass balances indicated fairly good recovery of radioactivity. For example, as shown in Table I (below) approximately 80% radioactivity was recovered on day 3 from a TCE mineralization assay.

TABLE I

Radioactivity Trapped in Organic and $CO_2$ Traps on Day 3 From a TCE Mineralization Assay[1]

| Trap No. | Trap Type | DPM |
|---|---|---|
| 1 | organic 1[2] | 71536 ± 200 |
| 2 | organic 2 | 4814 ± 50 |
| 3 | organic 3 | 50 ± 40 |
| 4 | $CO_2$ 1[3] | 4773 ± 90 |
| 5 | $CO_2$ 2 | 200 ± 40 |

[1]Mineralization was started with 5-day cultures of fungus by the addition of 10 ppm TCE and 100,000 dpm of $[^{14}C]$-TCE. The bottles were flushed with $O_2$ for 20 minutes. The outlet was connected in series to three organic traps and two $CO_2$ traps.
[2]Organic trap: 10 mL of Safety Solve Scintillation Cocktail.
[3]$CO_2$ trap: 10% ethanolamine, 40% methanol, 50% Safety Solve Scintillation Cocktail.

II. Results

Figure 2:
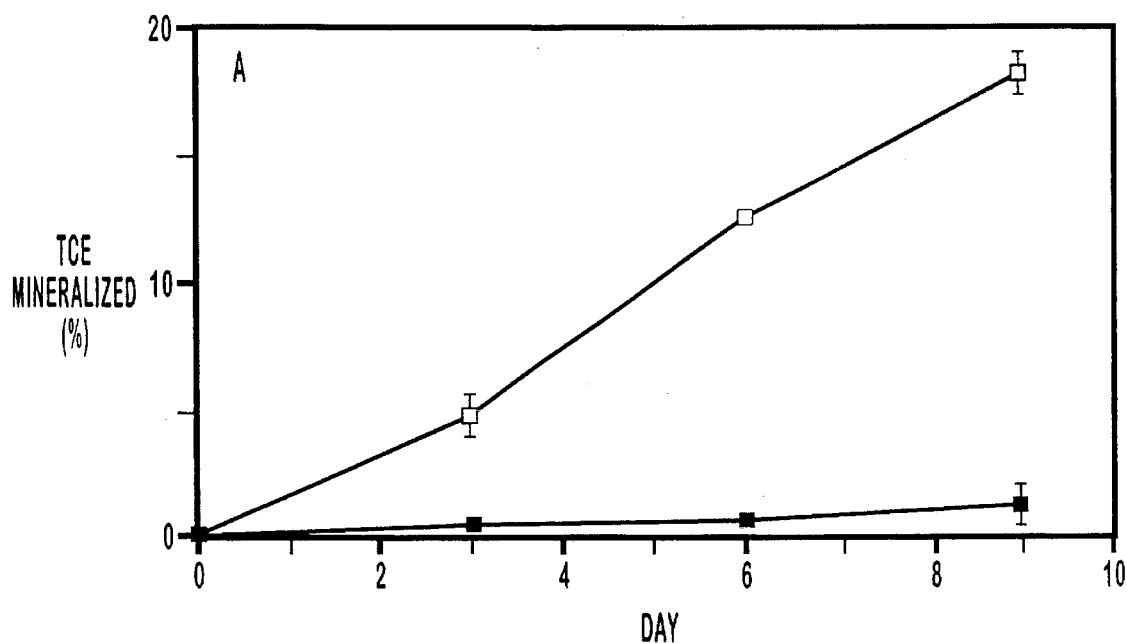
FIG. 2 illustrates mineralization of $\alpha\beta[^{14}C]$-TCE by nutrient nitrogen-limited, stationary cultures of *Phanerochaete chrysosporium*.
Figure 3:
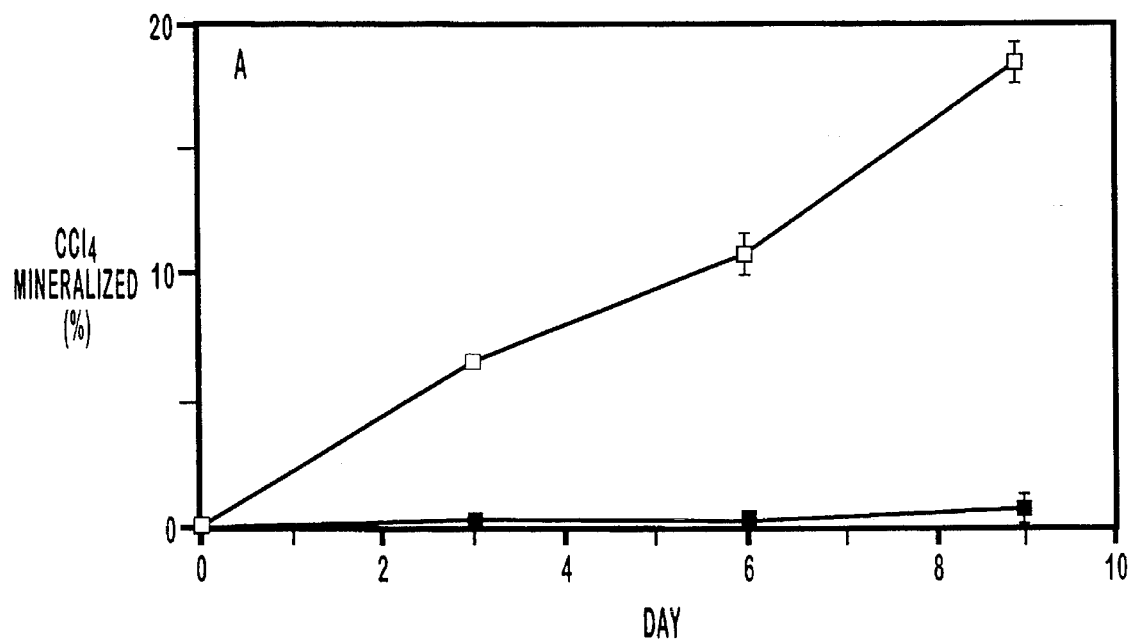
FIG. 3 illustrates mineralization of $[^{14}C]$-$CCl_4$ by nutrient nitrogen-limited, stationary cultures of *Phanerochaete chrysosporium*.

Mineralization of TCE and $CCl_4$. Both TCE and $CCl_4$ were mineralized by the fungus. As shown in FIG. 2, one-fifth (20.3%) of the initial concentration of TCE (10ppm) could be detected as $^{14}CO_2$ in a 9-day period. As shown in FIG. 3, 18.8% of 10 ppm $CCl_4$ was mineralized. Incubations were carried out in triplicate in nutrient nitrogen-limited stationary cultures of *Phanerochaete chrysosporium* at 37° as described above. The open square (□) values designate the accumulative percent of chemical converted to $CO_2$, normalized for loss of material as described above. The closed diamond (♦) values designate the mineralization observed in non-ligninolytic cultures of *P. chrysosporium*. The error bars (standard deviation) are within the figure symbols in some cases.

The radioactivity trapped in the organic and $CO_2$ traps for a typical mineralization assay are shown for TCE on day 3 in Table I (above). Background radiation observed in the third organic trap (50±40 dpm) immediately preceding the $CO_2$ trap indicates that the radioactivity associated with the $CO_2$ trap was not due to volatile halocarbon. The identity of the $^{14}CO_2$ was further confirmed by precipitation with $BaCl_2$ and quantitation of the radioactivity in the washed $BaCO_3$ precipitate.

Figure 4A:
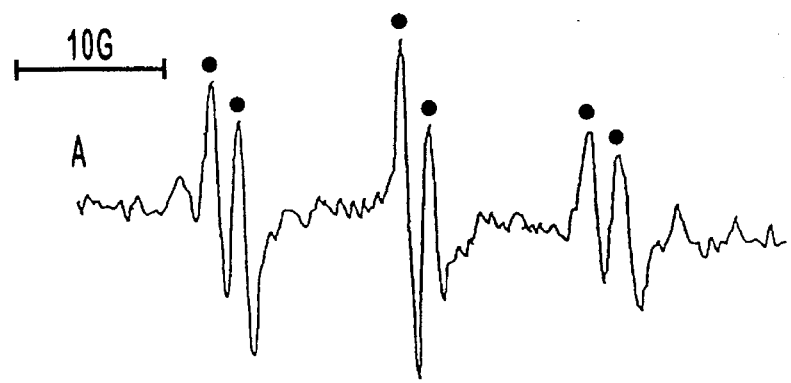
FIG. 4A shows the mixed ESR spectra of $PBN-CHCl_2$ and PBN-EDTA-derived radical adducts obtained from a reaction mixture containing LiP, $H_2O_2$, VA, EDTA, $CHCl_3$, and the spin trap α-phenyl-N-tert-butylnitrone (PBN).
Figure 4B:
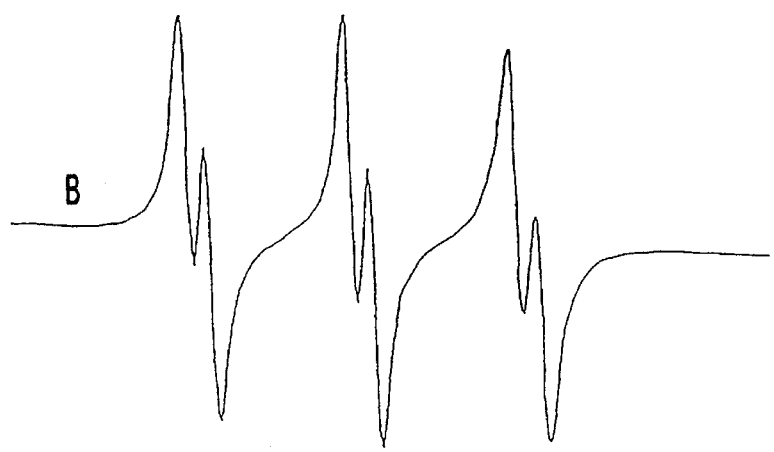
FIG. 4B shows the ESR spectra of $PBN-CHCl_2$ radical adduct obtained when $CHCl_2Br$ was substituted for $CHCl_3$ in a reaction mixture as described for FIG. 4A.
Figure 4C:
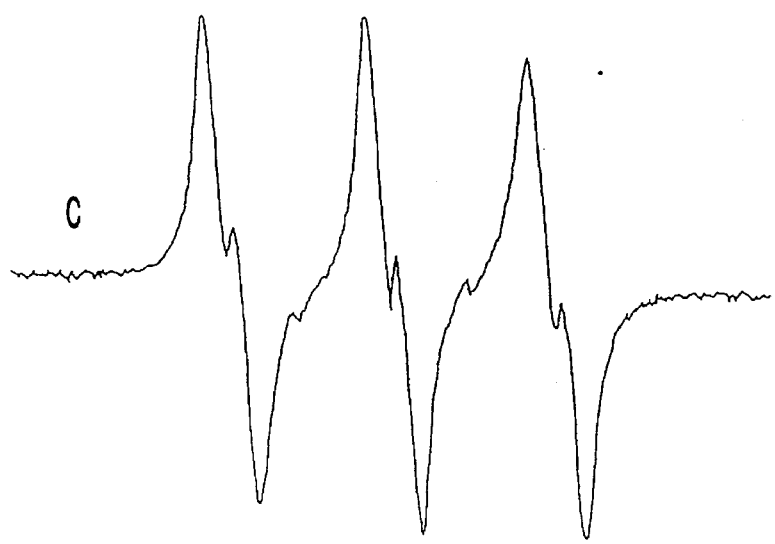
FIG. 4C shows the ESR spectra of $PBN-CHCl_2$ radical adduct obtained when sodium oxalate was substituted for EDTA as the reductant in a reaction mixture as described for FIG. 4B.

ESR Experiments. FIG. 4 demonstrates the presence of the dichloromethyl radical from the reduction of $CHCl_3$ to the dichloromethyl radical in various reaction mixtures. Spectrometer settings for the data shown in FIGS. 4A, 4B, and 4C were as follows: modulation amplitude, 1 G; time constant, 5.12 ms; scan time, 5.12 ms; microwave power 20 mW; and receiver gain, 1×10$^4$. As shown in FIG. 4A, a reaction mixture containing 1 µM LiP, 500 µM $H_2O_2$, 1 mM VA, 4 mM EDTA, 1% $CHCl_3$, and 80 mM of the spin trap PBN in 100 mM Chelex-treated sodium phosphate buffer, pH 6.0, produced a mixed ESR spectrum comprising predominantly PBN-$CHCl_2$ but with a small amount of PBN-EDTA-derived radical adducts. The filled circles (●) indicate the line assigned to the predominant (PBN-$CHCl_2$) spin adduct. An identical spectrum was obtained when the reaction mixture was purged with argon. The ESR hyperfine splitting constants for the halocarbon spin adduct, PBN-$CHCl_2$, were $a_N$=13.8 G and $a_H^\beta$=2.0 G.

When $CHCl_3$ was omitted from the reaction mixture, only EDTA-derived radicals were observed, as previously reported. Shah, M. M., et al., *J. Biol. Chem.*, On the Mechanism of Inhibition of the Veratryl Alcohol Oxidase Activity of Lignin Peroxidase H2 by EDTA, *J. Biol. Chem.*, 267:21564–69 (October 1992). When the reaction mixture was saturated with oxygen or if EDTA was omitted, no PBN adduct was observed.

To confirm the identity of the dichloromethyl radical spin adduct, 1% $CHCl_2Br$ was substituted for the 1% $CHCl_3$ in an identical reaction mixture. The rationale for this experiment was that, since the rate of debromination should be much higher than the rate of dechlorination, more of the halocarbon radical would be generated and hence interference from the PBN-EDTA derived radical would decrease. In addition, the same PBN-$CHCl_2$ radical adduct, with identical hyperfine splitting constants, would be expected from reductive debromination of $CHCl_2Br$ as from reductive dechlorination of $CHCl_3$ thereby confirming the identity of the radical. As shown in FIG. 4B, a single carbon-centered radical adduct spectrum was obtained. The hyperfine splitting constants were identical to those of the $CHCl_3$-derived radical adduct. The ratio of the nitrogen splitting to the hydrogen splitting for the PBN-$CHCl_2$ radical adduct, ($a_N/a_H^\beta$=6.9) was as reported previously. Davies, M. J., et al., *Chem.-Biol. Interact.*, 58:137–147 (1986). Moreover, as shown in FIG. 4C, when 10 mM sodium oxalate was substituted for EDTA as the reductant in the same reaction mixture with $CHCl_2Br$, the debrominated dichloromethyl radical, with the same hyperfine splitting constants, was observed. When any of the reactants (i.e., EDTA or oxalate, VA, $H_2O_2$, or LiP) were omitted, the dichloromethyl radical was not observed.

To further confirm the identity of the spin adduct, [$^{13}$C]-$CHCl_3$ was used. Since $^{13}$C has a spin quantum number of 0.5, additional hyperfine splitting occurs due to the interaction of the unpaired electron with this nucleus. This yields a 12-line spectrum as compared to a 6-line spectrum for [$^{12}$C]-$CHCl_3$. As expected, additional hyperfine splittings were observed (data not shown). The spectrum obtained was a mixture of PBN-EDTA derived radical adducts and predominantly the PBN-[$^{13}$C]$CHCl_2$ radical adduct. The splitting constants for the PBN-[$^{13}$C]$CHCl_2$ radical adduct were $a_N$=13.8 G, $a_H^\beta$=2.0 G, and $a_\beta^{13}C$=9.2 G. This radical adduct was not obtained in the absence of [$^{13}$C]-$CHCl_3$.

Figure 5A:
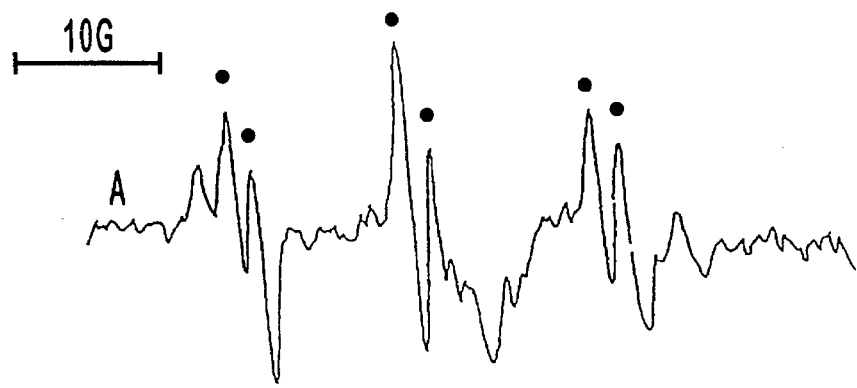
FIG. 5A shows the mixed ESR spectra of $PBN-CH_2Cl$ and PBN-EDTA-derived radical adducts obtained from a reaction mixture containing LiP, $H_2O_2$, VA, EDTA, $CH_2Cl_2$, and the spin trap α-phenyl-N-tert-butylnitrone (PBN).

As shown in FIG. 5, when dichloromethane replaced chloroform in the reaction mixture, a different carbon-centered PBN radical adduct was observed. Spectrometer settings for the data shown in FIGS. 4A, 4B, and 4C were as follows: modulation amplitude, 1 G; time constant, 5.12 ms; scan time, 5.12 ms; microwave power 20 mW; and receiver gain, 1×10$^4$. As shown in FIG. 5A, a reaction mixture containing 1 µM LiP, 500 µM $H_2O_2$, 1 mM VA, 4 mM EDTA, 1% $CH_2Cl_2$, and 80 mM of the spin trap PBN in 100 mM Chelex-treated sodium phosphate buffer, pH 6.0, produced a mixed ESR spectrum comprising predominantly PBN-$CH_2Cl$ and PBN-EDTA-derived radical adducts. An identical radical adduct spectrum could also be observed under anaerobic conditions. The ESR hyperfine splitting constants for the $CH_2Cl_2$-derived radical adduct were $a_N$=13.7 G, $a_H^\beta$=2.2 G. This radical adduct was not observed when $CH_2Cl_2$ was left out of the reaction mixture or when the reaction mixture was saturated with $O_2O$.

Figure 5B:
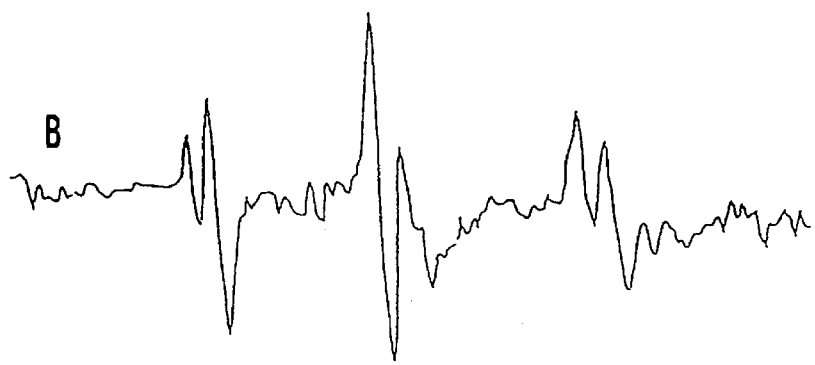
FIG. 5B shows the ESR spectra of $PBN-CH_2Cl$ radical adduct obtained when $CH_2ClBr$ was substituted for $CH_2Cl_2$ in a reaction mixture as described for FIG. 5A.
Figure 5C:
FIG. 5C shows the ESR spectra of $PBN-CH_2Cl$ radical adduct obtained when sodium oxalate was substituted for EDTA as the reductant in a reaction mixture as described for FIG. 5B.

For the reasons explained previously, 1% $CH_2ClBr$ was substituted for $CH_2Cl_2$ in an identical reaction mixture. As shown in FIG. 5B, a single carbon centered radical adduct was observed which had the same ESR hyperfine splitting constants as the $CH_2Cl_2$-derived radical adduct. The ratio of nitrogen splitting constant to the hydrogen splitting constant was 6.2. When control experiments were performed, by leaving out LiP, $H_2O_2$, VA or reductant from the reaction mixture, the monochloromethyl radical was not observed. Moreover, as shown in FIG. 5C, when 10 mM sodium oxalate was substituted for EDTA as the reductant in the same reaction mixture with $CHCl_2Br$, the same radical adduct with identical hyperfine splitting constants was observed.

The PBN-$CH_2Cl$ radical adduct identity was also confirmed by using [$^{13}$C]$CH_2Cl_2$. Additional hyperfine splittings were observed which were attributed to the $^{13}$C nucleus (data not shown). The hyperfine splitting constants for PBN-[$^{13}$C]$CH_2Cl$ radical adduct were $a_N$=13.7 G, $a_H^\beta$= 2.2 G, and $a_\beta^{13}C$=9.1 G, When control experiments were performed by omitting [$^{13}$C]-$CH_2Cl_2$ from the reaction mixture, only PBN-EDTA-derived radical adducts spectra were observed.

Dehalogenated radicals of trichloroethylene and 1,1,1-trichloroethane were also detected from reaction mixtures containing 1% of the halocarbon of interest, 1 µM LiP, 500 µM $H_2O_2$, 1 mM VA, either 4 mM EDTA or 15 mM sodium oxalate, and 80 mM of the spin trap PBN in 100 mM Chelex-treated sodium phosphate buffer, pH 6.0. Table II tabulates data with respect to the various PBN-halocarbon radical adducts.

TABLE II

ESR Hyperfine Splitting Constants of PBN-Halocarbon Radical Adducts

| Halocarbon | $a_N$ (Gauss) | $a_H^\beta$ (Gauss) | NoH[a] | Reduction Potential[b] (V vs NHE) |
|---|---|---|---|---|
| $CCl_4$[c] | 14.0 | 1.80 | 7.7 | −1.0 |
| $CHCl_3$ | 13.8 | 2.00 | 6.9 | −1.76 |
| $CHCl_2Br$ | 13.8 | 2.00 | 6.9 | NA[d] |
| $CH_2Cl_2$ | 13.7 | 2.20 | 6.2 | −2.2 |
| $CH_2ClBr$ | 13.7 | 2.20 | 6.2 | NA |
| TCE[e] | 13.3 | 2.60 | 5.1 | NA |
| TCA[f] | 13.3 | 1.75 | 7.6 | NA |

[a]$a_N/a_H^\beta$
[b]Wagman, D. D., et al., J. Phys. Chem. Ref. Data, 11:1188–1195 (1982).
[c]Shah, M. M., et al., Biochem. Biophys. Res. Commun., 191:887–892 (1993).
[d]Not available.
[e]Trichloroethylene.
[f]1,1,1-trichloroethane.

Figure 6:
FIG. 6 shows the ESR spectra of $DMPO-CO_2^-$ radical adduct obtained from a reaction mixture containing LiP, $H_2O_2$, VA, oxalate, and the spin trap 5,5-dimethyl-1-pyrroline-N-oxide (DMPO).

Since oxalate was able to act as an electron donor and mediate the reduction of halocarbons, evidence for the presence of $CO_2^-$ radical, a strong reductant ($E^{108}$=−1.9 V vs NHE), in the reaction mixtures was obtained by ESR spin trapping with the spin trap DMPO. The reaction mixture contained 1 μM LiP, 500 μM $H_2O_2$, 1 mM VA, 10 mM oxalate, and 10 mM DMPO in phosphate buffer, pH 6.0. As shown in FIG. 6, the ESR spectrum for the DMPO-$CO_2$ radical adduct was obtained. The ESR hyperfine splicing constants were $a_N$=15.7 G, $a_H^\beta$=18.7 G which are identical to those reported in the literate. Popp, J. L., et al., *Biochemistry* 29:10475–10480 (1990). When oxalate was omitted from the reaction mixture, no radical adduct signal was obtained. When 1% $CCl_4$ was added to the reaction mixture, no radical adduct signal was obtained. This was probably due to the scavenging of the $CO_2^-$ by $CCl_4$. The resultant trichloromethyl radical does not react readily with DMPO. Oldenuis, R., et al., *Appl. Environ. Microbiol.*, 55:2819–2826 (1989).

III. Discussion

The results of our investigation indicated that TCE (10 ppm) and $CCl_4$ (10 ppm) could be mineralized by ligninolytic whole cultures of *P. chrysosporium* under aerobic conditions. This finding is significant because near environmental levels of contamination 10 ppm) were converted to an environmentally acceptable biotransformation product. The extent of mineralization could not be determined as these chemicals are quite volatile and are removed during gas exchange in the mineralization assay. The mineralization studies were therefore limited to a maximum of 9 days, the maximum time that the flasks could be sealed and still be aerobic. However, the rates of mineralization, corrected for the amount of chemical lost during incubation, were linear for 9 days.

The magnitude of the $a_H^\beta$ (ESR hydrogen splitting) for the PBN adducts derived from the different halocarbons were inversely proportional to the degree of halogenation (i.e., $a_H^\beta$, PBN-$CH_2Cl$>PBN-$CHCl_2$>PBN-$CCl_3$), as would be predicted from the decreased inductive effect with fewer Cl atoms in the adduct. Furthermore, the bulk of the spin-trapped radical in the spin adduct also influences the β-H splitting. Oldenhuis, R., et al., *Appl. Environ. Microbiol.*, 55:2819–2826 (1989). The magnitude of the β-H splittings depends on the "dihedral" angle between the C—H bond and p-orbital on the nitrogen in the spin trap. When the angle is large, the splitting is small; conversely, when the dihedral angle is small, the splitting is large. Hence, it can be predicted that for smaller spin-trapped groups the β-H splitting would be large, as was observed.

We also obtained evidence for carboxylate anion radical in our reaction system. The reduction potential of the carboxylate anion radical, $CO_2^-$, (−1.9 V vs NHE) is sufficient to dehalogenate $CHCl_3$ (−1.76 V vs NHE). Wagman, D. D., et al., *J. Phys. Chem. Ref. Data*, 11:1188–1195 (1982). This can also account for the dehalogenation of dichloromethane (−1.4 V vs NHE). We further believe that dehalogenation may be favored because one product of the reaction is carbon dioxide.

Since all of the spin trapping experiments were carried out under aerobic conditions, halocarbon reduction by superoxide anion radical ($O_2^-$) cannot be precluded. It has been reported that $O_2^-$ is capable of dehalogenating aliphatic and aromatic halocarbons in aprotic solvents. Roberts, J. L., et al., *J. Am. Chem. Soc.*, 105:7691–7696 (1983). Also, superoxide anion radical formation is known to be catalyzed by LiP. Bart, D. P., et al., *Arch. Biochem. Biophys.*, 298:480–485 (1992). However, it is theorized that it is not the reductant because its reduction potential, −0.35 V vs NHE, does not appear sufficient to carry out these reductions. Furthermore, the dehalogenated radicals could be trapped under anaerobic conditions (data not shown). Oxygen will nevertheless compete with the halocarbons for reduction, and hence lower $O_2$ concentrations would be expected to favor the reductive dehalogenation by the proposed mechanism. This was observed as no dehalogenation took place with saturated $O_2$ solution. At normal oxygen concentrations, however, the carboxylate anion radical would be able to dehalogenate the aliphatic halocarbons as was demonstrated by the ESR experiments. The dehalogenated and possibly less toxic compounds can then be mineralized by the fungus.

IV. Degradation of Methylene Chloride.

Utilizing the conditions described above, methylene chloride is reductively dehalogenated to methane. It is believed that this reductive dehalogenation is caused by a mediator such as the anion radical of EDTA or the carboxylate anion formed from the decarboxylation of the anion radical of oxalate. It is believed that the methane formed by reductive dechlorination will in turn be degraded to carbon dioxide.

Summary

From the foregoing, it should be understood that TCE, $CCl_4$, and other very highly oxidized halocarbons can be reductively dehalogenated and the reduced products mineralized by ligninolytic cultures of *P. chrysosporium*. Reductive dehalogenation of both $CCl_4$ and $CH_2Cl_2$ teaches that halocarbons which have reduction potentials between −0.229 and −1.4 V can be dehalogenated. These chemicals include known environmental pollutants like DDT, chlorofluorocarbons, Dicofol, methoxychlor, trichloroethanol, TCE, and TCA. Janzen, E. G., et al., *Environ. Health Perspect.*, 64:151–170 (1985). Reduced products of DDT (DDD) and Dicofol (FW-152) have been isolated from ligninolytic cultures of *P. chrysosporium*, Janzen, E. G., et al., *Free Radical Res. Commun.*, 4:359–369 (1987), suggesting that this reductive mechanism may be involved in the mineralization of these chemicals by the fungus.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A method of degrading an aliphatic halocarbon, the method comprising the steps of:

(1) providing a reaction mixture containing:

(a) a peroxidase to serve as a free radical generating catalyst;

(b) a suitable mediator which can be oxidized by said peroxidase to form the free radical of said mediator, said free radical of said mediator being an oxidizing agent;

(c) a suitable reductant which can be oxidized by said free radical of said mediator to form the free radical of said reductant, said free radical of said reductant being a reducing agent;

(2) exposing an aliphatic halocarbon to the reaction mixture; and (3) allowing the aliphatic halocarbon to become dehalogenated through reaction with a reducing agent generated within the reaction mixture.

2. A method as described in claim 1 wherein said reaction mixture provided in step (1) further comprises hydrogen peroxide.

3. A method as described in claim 1 wherein said reductant is EDTA and wherein said EDTA reacts with said free radical of said mediator to form the anion radical of EDTA.

4. A method as described in claim 3 wherein said anion radical of EDTA reductively dehalogenates the aliphatic halocarbon in a reaction which generates carbon dioxide.

5. A method as described in claim 1 wherein said peroxidase, mediator, and reductant are provided by a white rot fungus.

6. A method as described in claim 5 wherein said reductant is oxalate and wherein said oxalate reacts with said free radical of said mediator to form the anion radical of oxalate.

7. A method as described in claim 6 wherein said anion radical of oxalate reacts with carbon dioxide to form the carboxylate anion radical.

8. A method as described in claim 7 wherein said carboxylate anion radical reductively dehalogenates the aliphatic halocarbon in a reaction which generates carbon dioxide.

9. A method as described in claim 1 wherein the aliphatic halocarbon is chloroform.

10. A method as described in claim 1 wherein the aliphatic halocarbon is dichloromethane.

11. A method as described in claim 1 wherein the aliphatic halocarbon is trichloroethylene.

12. A method as described in claim 1 wherein the aliphatic halocarbon is 1,1,1-trichloroethane.

13. A method as described in claim 1 wherein the aliphatic halocarbon is methylene chloride.

14. A method of degrading an aliphatic halocarbon, the method comprising the steps of:
   (1) providing a reaction mixture containing:
      (a) hydrogen peroxide;
      (b) a peroxidase to serve as a free radical generating catalyst;
      (c) a suitable mediator which can be oxidized by said peroxidase to form the free radical of said mediator, said free radical of said mediator being an oxidizing agent;
      (d) EDTA as a reductant which can be oxidized by said free radical of said mediator to form the anion radical of EDTA;
   (2) exposing an aliphatic halocarbon to the reaction mixture; and
   (3) allowing the aliphatic halocarbon to be reductively dehalogenated through reaction with said anion radical of EDTA thereby generating carbon dioxide.

15. A method as described in claim 14 wherein said peroxidase is provided by a white rot fungus.

16. A method as described in claim 14 wherein the mediator is provided by a white rot fungus.

17. A method as described in claim 16 where the mediator is veratryl alcohol.

18. A method as described in claim 14 wherein the hydrogen peroxide is provided by a white rot fungus.

19. A method of degrading an aliphatic halocarbon, the method comprising the steps of:
   (1) providing a reaction mixture containing:
      (a) hydrogen peroxide;
      (b) a peroxidase to serve as a free radical generating catalyst;
      (c) a suitable mediator which can be oxidized by said peroxidase to form the free radical of said mediator, said free radical of said mediator being an oxidizing agent;
      (d) oxalate as a reductant which can be oxidized by said free radical of said mediator to form the anion radical of oxalate;
      (e) carbon dioxide;
   (2) allowing the anion radical of oxalate to react with carbon dioxide to form carboxylate anion radical;
   (3) exposing an aliphatic halocarbon to the reaction mixture; and
   (4) allowing the aliphatic halocarbon to become reductively dehalogenated through reaction with said carboxylate anion radical thereby generating carbon dioxide.

20. A method as described in claim 19 wherein said oxalate is provided by a white rot fungus.

21. A method as described in claim 19 wherein said peroxidase is provided by a white rot fungus.

22. A method as described in claim 19 wherein the mediator is provided by a white rot fungus.

23. A method as described in claim 22 wherein the mediator is veratryl alcohol.

24. A method of degrading an aliphatic halocarbon, the method comprising the steps of:
   (1) providing a reaction mixture containing a white rot fungi, said white rot fungi producing peroxidases, hydrogen peroxide, veratryl alcohol, oxalate and carbon dioxide;
   (2) exposing an aliphatic halocarbon to the reaction mixture; and
   (3) allowing the aliphatic halocarbon to be reductively dehalogenated through reaction with said reaction mixture thereby generating carbon dioxide.

25. A method of degrading an aliphatic halocarbon, the method comprising the steps of:
   (1) providing a reaction mixture containing a white rot fungi, said white rot fungi producing peroxidases, hydrogen peroxide, and veratryl alcohol;
   (2) providing EDTA;
   (3) exposing an aliphatic halocarbon to the reaction mixture; and
   (3) allowing the aliphatic halocarbon to be reductively dehalogenated through reaction with said reaction mixture thereby generating carbon dioxide.

26. A reaction mixture useful for degrading aliphatic halocarbons comprising:
   (a) a peroxidase to serve as a free radical generating catalyst;
   (b) a suitable mediator which can be oxidized by said peroxidase to form the free radical of said mediator, said free radical of said mediator being an oxidizing agent; and
   (c) a suitable reductant which can be oxidized by said free radical of said mediator to form the free radical of said reductant, said free radical of said reductant being a reducing agent.

27. A reaction mixture as described in claim 26 wherein said reaction mixture further comprises hydrogen peroxide.

28. A reaction mixture as described in claim 27 wherein said hydrogen peroxide is provided by a white rot fungus.

29. A reaction mixture as described in claim 26 wherein said reductant is EDTA and wherein said EDTA reacts with said free radical of said mediator to form the anion radical of EDTA.

30. A reaction mixture as described in claim 26 wherein said reductant is provided by a white rot fungus.

31. A reaction mixture as described in claim 30 wherein said reductant is oxalate and wherein said oxalate reacts with said free radical of said mediator to form the anion radical of oxalate.

32. A reaction mixture as described in claim 26 wherein said peroxidase is provided by a white rot fungus.

33. A reaction mixture as described in claim 26 wherein the mediator is provided by a white rot fungus.

34. A reaction mixture useful for degrading aliphatic halocarbons comprising:

hydrogen peroxide;

a peroxidase to serve as a free radical generating catalyst;

a suitable mediator which can be oxidized by said peroxidase to form the free radical of said mediator, said free radical of said mediator being an oxidizing agent; and EDTA as a reductant which can be oxidized by said free radical of said mediator to form the anion radical of EDTA.

35. A reaction mixture useful for degrading aliphatic halocarbons comprising:

hydrogen peroxide;

a peroxidase to serve as a free radical generating catalyst;

a suitable mediator which can be oxidized by said peroxidase to form the free radical of said mediator, said free radical of said mediator being an oxidizing agent;

oxalate as a reductant which can be oxidized by said free radical of said mediator to form the anion radical of oxalate; and carbon dioxide.

* * * * *

UNITED STATES PATENT AND TRADEMARK OFFICE
CERTIFICATE OF CORRECTION

PATENT NO. : 5,556,779
DATED : September 17, 1996
INVENTOR(S) : Aditya Khindaria, et al It is certified that error appears in the above-identified patent and that said Letters Patent is hereby corrected as shown below:

Column 2, line 46, "LIP" should be --LiP--
Column 6, line 59, "H2 02" should be --$H_2O_2$--
Column 8, line 7, "CC14" should be --$CCl_4$--
Column 8, line 37, "LIP" should be --LiP--
Column 8, line 39, "LiPo(ox)" should be --LiP9(ox)--
Column 8, line 62, "Peroxidase.H2" should be --Peroxidase H2--
Column 9, line 49, "H2 02" should be --$H_2O_2$--
Column 11, line 3, "1 G" should be --1G--
Column 11, line 48, "H2 02" should be --$H_2O_2$--
Column 11, line 66, "1 G" should be --1G--
Column 12, line 12, "O20." should be --$O_2$--
Column 12, line 65, " (E108=-1.9V vs NHE)" should be --(E=-1.9V vs NHE)--
Column 13, line 32, "ofhalogenation" should be --of halogenation--
Column 13, line 61, "Bart" should be -- Barr--

Signed and Sealed this

Twenty-first Day of April, 1998

Attest:

BRUCE LEHMAN

*Attesting Officer*  *Commissioner of Patents and Trademarks*